US005612061A

United States Patent [19]
Rabkin

[11] Patent Number: 5,612,061
[45] Date of Patent: Mar. 18, 1997

[54] COMPOSITION AND METHOD FOR THE TREATMENT OF PREMENSTRUAL SYNDROME

[76] Inventor: Simon W. Rabkin, 3564 Quesnel Dr., Vancouver, B.C., Canada, V6L 2W6

[21] Appl. No.: 323,080

[22] Filed: Oct. 14, 1994

[51] Int. Cl.$^6$ ............ A61K 31/16; A61K 31/165; A61K 33/06; A61K 33/42; A61K 31/13; A61K 31/152

[52] U.S. Cl. ............ 424/602; 424/603; 424/678; 424/682; 424/683; 424/686; 424/687; 424/688; 424/689; 424/692; 424/693; 424/694; 424/696; 424/697; 514/23; 514/25; 514/262; 514/263; 514/264; 514/423; 514/460; 514/557; 514/558; 514/625; 514/629; 514/667; 514/899

[58] Field of Search ............ 424/682, 683, 424/686, 687, 688, 689, 692, 693, 694, 696, 697, 602, 603, 678; 514/23, 25, 262–264, 423, 460, 557–558, 625, 629, 667, 899

[56] References Cited

U.S. PATENT DOCUMENTS

| | | | |
|---|---|---|---|
| 4,946,679 | 8/1990 | Thys-Jacobs | 424/682 |
| 5,011,688 | 8/1991 | Calam et al. | 424/195.1 |
| 5,155,105 | 10/1992 | Jones et al. | 514/223.5 |
| 5,296,241 | 3/1994 | Brimberg et al. | 424/682 |

OTHER PUBLICATIONS

Premenstrual and Menstrual Symptom Clusters and Response to Calcium Treatment Psychopharmacology Bulletin, vol. 27, No. 2, 1991, (Dr. Jose Ma. J. Alvir. and Susan Thys–Jacobs) pp. 145–148.

Oral Magnesium Sucessfully Relieves Premenstrual Mood Changes. (Fabio Facchinetti, MD, Paola Borella, MD, Gragia Sances, MD, Loredana Fioroni, MD, Rossella Nappi, MD and Andrea Genazzani, MD, Obstetrics & Gynecology, vol. 78, No. 2, 1991, pp. 177–181.

The Effect of a Nutritional Supplement, Optivite for Women, on Premenstrual Tension Syndromes. (Fuchsn. Ph.D., Hakim and Abraham), Journal of Applied Nutrition, vol. 37, No. 1, 1985, pp. 1–11.

Clinician's Approach to the Diagnosis and Management of Premenstrual Syndrome (Susan B. Johnson, MD), Clinical Ob. and Gyn., vol. 35(3), 1992, pp. 637–657.

Calcium Supplementation in Premenstrual Syndrome (Susan Thys–Jacobs, Silvio Ceccarelli, Arlene Bierman, Henry Weismam et al.), J. Gen. Int. Med., vol. 4, 1989, pp. 183–189.

Caffiene–Containing Beverages, TotalFluid Consumption, and Premenstrual Syndrome (Annette MacKay Rossignol and Heinke Bonnlander, RN), Am. J. Public Health, 1990, p. 1106.

The Menstrual Cycle, Physiology, Reproductive Disorders and Infertility (Michael Ferin, Raphael Jewelewicz and Michelle Warren), Oxford University Press, New York, 1993, pp. 198–204 and 245–246.

The Effect of a Nutritional Supplement, Optivite for Women, on Premenstrual Tension Syndromes (Chakmakjian, Higgins and Abraham), J. Applied Nutrition, vol. 37(1), 1985, pp. 12–17.

Effect of a Nutritional Supplement on Premenstrual Symptomatology in Women with Premenstrual Syndrome: A double–Blind Longitudinal Study (London, Bradley, and Chiamori), Journal of the American College of Nutrition, vol. 10, No. 5, 1991, pp. 495–499.

*Primary Examiner*—John Pak

[57] ABSTRACT

A composition for the treatment of premenstrual syndrome comprising an effective amount of calcium, magnesium, an analgesic and a diuretic sufficient to reduce the symptoms of premenstrual syndrome.

10 Claims, No Drawings

COMPOSITION AND METHOD FOR THE TREATMENT OF PREMENSTRUAL SYNDROME

FIELD OF THE INVENTION

The present invention relates to therapeutic compositions and methods and in particular compositions and methods for treatment of an individual exhibiting symptoms of premenstrual syndrome.

BACKGROUND OF THE INVENTION

The premenstrual syndrome (PMS) is a cyclic disorder occurring during the late luteal phase of the menstrual cycle and ending once menstrual flow returns. The condition was first described over sixty years ago as "premenstrual tension syndrome". The most common symptoms of PMS include bloating, abdominal discomfort, change in appetite, breast tenderness, and headache. Behavioral changes include fatigue, depression, anxiety, irritability, anger, confusion, and social withdrawal.

The symptoms of PMS are often so severe and widespread that the American Psychitric Association has formally identified the diagnostic criteria for PMS in *Diagnostic and Statistical Manual of Mental Disorders.*

The specific etiology of PMS remains unknown, although many theories have been proposed. These include: hormonal imbalances, hormonal deficiencies, vitamin deficiencies, disturbances of the autonomic nervous system, salt and water imbalances, altered endogenous opiates and psychosomatic dysfunction. Up to now, investigative studies of etiology have been inconclusive and sometimes conflicting. M. Ferin, R. Jewelewicz and M. Warren, *The Menstrual Cycle: Physiology, Reproductive Disorders, and Infertility,* pp. 198–204 (1993). Most likely, PMS is multifactorial and probably also involves changes in neurohormones and neurotransmitters, which are not easily documented in humans.

Numerous attempts have been made to develop an effective treatment for the symptoms of PMS. Dietary modification including reduction of salt, alcohol, and beverages containing caffeine have been suggested. Pharmacologic intervention is commonly used, especially progesterone therapy and hypothalamic-pituitary-ovarian axis suppressors.

Nonprescription pharmacologic compositions have also been made available. Most provide aspirin or acetaminophen as an analgesic for diminishing menstrual pain. Calcium has also been found to be an effective treatment, especially in regard to premenstrual pain and water retention. S. Thys-Jacobs, S. Ceccarelli, A. Bierman, H. Weisman, M. A. Cohen and J. Alvir, *Calcium supplementation in premenstrual syndrome: A randomized crossover trial,* J. Gen. Int. Med. 4:183–189,(1989). Magnesium supplementation has been documented to relieve certain other symptoms of PMS including pain, negative affect and arousal i.e. mood fluctuations although other symptoms were unaffected. F. Fancchinetti, P. Borella, G. Sances, L. Fioroni, R. Nappi and A. R. Genazzani, *Oral Magnesium Successfully Relieves Premenstrual Mood Changes,* Obstetrics & Gynecology 78:177–181,(1991).

None of the prior art nonprescription compositions have been found to be completely effective. Although they alleviate certain symptoms of PMS, other symptoms remain untreated or show little or no improvement. Further, at least some prior art compositions are known to contain ingredients that cause undesirable side effects. For example, U.S. Pat. No. 5,001,688 (Calam et al.) contains both ethyl alcohol and an antihistamine which can cause drowsiness. Further, none of the active ingredients reduce negative effect, fatigue or bloating. Midol, a commercially available nonprescription composition has contained aspirin along with caffeine and an antispasmodic ingredient. Recent investigations have indicated that consumption of caffeine containing beverages is strongly related to the prevalence and severity of PMS and should therefore be avoided. A. Mackay—Rossignol and H. Bonnlander, *Caffeine-Containing Beverages, Total Fluid Consumption., and Premenstrual Syndrome,* Am. J. Pub. Health, pg.1106 (1990).

Thus, a patient is often left with no other choice than to simultaneously take different compositions in an attempt to relieve all of the various symptoms while at the same time try to avoid those known to produce side effects. For obvious reasons such self-medication is undesirable. Even the relatively benign ingredients found in nonprescription drugs present the potential for an overdose. Further, interaction between active ingredients found in different compositions can actually reduce the overall effectiveness of treatment, especially if the active ingredients operate by a similar mechanism.

Since PMS encompasses a broad spectrum of symptomatology, physicians are faced with a variety of options when deciding on a safe program of treatment. A need has therefore arisen for a single nonprescription composition that will provide a broad therapeutic spectrum while exhibiting greater overall activity.

Against this background the present invention was developed.

OBJECTS AND SUMMARY OF THE INVENTION

It is an object of the present invention to provide a nonprescription pharmaceutical composition for the relief of the broad spectrum of symptoms associated with premenstrual syndrome (PMS).

It is another object of the present invention to provide a nonprescription pharmaceutical composition for the relief of PMS within a single formulation thereby eliminating the need for ingesting multiple medications.

Another object of the present invention is to provide a composition for the treatment of PMS symptoms that achieves enhanced compliance from the patient and therefore better results because each of the active ingredients required to treat the various symptoms are provided within a single formulation.

It is yet another object of the present invention to provide a nonprescription composition for the treatment of PMS containing two mineral replacements along with an analgesic and a non-caffeine diuretic to provide combination therapy having a broad therapeutic spectrum.

It is another object of the present invention to provide a single nonprescription pharmaceutical composition for the treatment of PMS containing multiple active ingredients which in combination have an overall synergistic effect providing improved therapeutic activity.

It is still another object of the present invention to provide a method for the treatment of premenstrual syndrome through the administration of two minerals, an analgesic and a diuretic.

In summary, the present invention provides a method for treating premenstrual syndrome comprising administering an effective amount of calcium, magnesium, an analgesic and a diuretic so that the symptoms of premenstrual syndrome are reduced.

The present invention is also directed to a composition for the relief of pain and discomfort associated with premenstrual syndrome comprising and effective amount of calcium, magnesium, an analgesic and a diuretic.

These and other objects of the present invention will become apparent from the following detailed description.

DETAILED DESCRIPTION OF THE INVENTION

The composition according to the present invention is a formulation including at least four separate active ingredients: (1) magnesium; (2) calcium; (3) an analgesic; and (4) a diuretic. Aspirin (acetylsalicylic acid), acetaminophen and ibuprofen are each effective analgesics within the scope of the present invention. The analgesic functions to relieve the symptoms of abdominal cramps, back pain and pain from swollen and tender breasts as well as headache pain. In a preferred embodiment, the analgesic acetaminophen is administered in a dose of about 500 mg. four times a day for a total of about 2000 mg/day.

The diuretic is provided to relieve symptoms related to water retention such as excessive water weight, bloating, swelling, painful breasts, cramps and tension. The preferred diuretic within the scope of the present invention is pamabrom, a theophylline derivative. In addition, ammonium chloride, an acid-forming salt may be used. As noted above, caffeine is not a preferred diuretic since it tends to extend the symptoms of PMS rather than provide relief. In the preferred embodiment, the diuretic is administered in a dose of about 25 mg four times a day for a total of about 100 mg/day.

Elemental magnesium ($Mg^{2+}$) is provided for relief of "negative affect" i.e. premenstrual mood fluctuations. Mg cation supplementation must be sufficient to increase the cation content in both the lymphocytes and polymorphonuclear cells. This generally means a dosage higher than the recommended dietary allowances set by the National Academy of Sciences but low enough to avoid the risk of overload. Applicant has determined that the magnesium cation be administered in a dose of about 100 mg of magnesium four times a day for a total of about 400 mg/day. Preferred sources of magnesium ion for oral ingestion include magnesium glucoheptonate, magnesium pyrrolidone carboxylic acid, magnesium gluconate, magnesium pyroglutamate and magnesium sulfate.

Elemental calcium ($Ca^{2+}$) provides relief for both the physical and behavioral symptoms of PMS. Behavioral symptoms are generally characterized as "negative affect". Within the meaning of the present invention these include depression, violent tendencies, crying, mood swings, irritability and nervousness. Physical symptoms treated by the calcium therapy according to the present invention include headache, back pain, water retention, abdominal bloating and cramps, breast tenderness and fatigue. Applicant has determined that the calcium be administered in a dose of about 300 mg four times a day for a total of about 1200 mg/day. In the preferred embodiment, the source of calcium for the formulation according to the present invention is in the form of calcium carbonate, calcium chloride, calcium glucoheptonate, calcium gluconate, calcium gluconogalactogluconate, calcium gluceptate, calcium lactate, calcium glubionate, calcium phosphate dibasic anhydrous, calcium phosphate dibasic dihydrate and calcium phosphate tribasic.

Both the magnesium and calcium within the scope of the present invention must be in a form to allow the ions to be readily adsorbed by the body. The above described calcium and magnesium compounds allow such absorption into the body. Antacid agents are to be avoided since magnesium or calcium cations are less readily adsorbed from such compounds.

A formulation according to the present invention may be summarized in Table 1 set forth below:

TABLE 1

| Ingredients | Amount in parts by weight ±20% |
|---|---|
| analgesic | 50.0 |
| diuretic | 4.0 |
| elemental calcium | 34.0 |
| elemental magnesium | 11.5 |

The specific formulation set forth above produces optimal therapeutic results within the permissible deviation indicated. However, certain individual ingredients may vary in amount and still produce satisfactory results. The following specific examples are representative of the composition according to the present invention:

| Ingredients | Amount in parts by weight |
|---|---|
| *Example 1* | |
| calcium carbonate | 300 mg |
| magnesium gluconate | 100 mg |
| acetaminophen | 500 mg |
| pamabrom | 25 mg |
| *Example 2* | |
| calcium carbonate | 300 mg |
| magnesium gluconate | 100 mg |
| acetaminophen | 500 mg |
| pamabrom | 50 mg |
| *Example 3* | |
| calcium carbonate | 300 mg |
| magnesium gluconate | 100 mg |
| ibuprofen | 400 mg |
| pamabrom | 25 mg |
| *Example 4* | |
| calcium carbonate | 300 mg |
| magnesium gluconate | 100 mg |
| ibuprofen | 400 mg |
| pamabrom | 50 mg |
| *Example 5* | |
| calcium carbonate | 300 mg |
| magnesium gluconate | 100 mg |
| aspirin | 400 mg |
| pamabrom | 25 mg |

| Example 6 Liquid Formulation | |
|---|---|
| Ingredients | Grams/L |
| $Mg^{2+}$ (100 mg of mag. ion/fl oz.) | 35.2 |
| $Ca^{2+}$ (300 mg of $CaCO_3$/fl oz.) | 10.65 |
| Acetominophen (500 mg/fl oz.) | 17.3 |
| Pamabrom (25 mg/fl oz.) | 0.85 |
| Sucrose | balance |
| Sodium Banzoate | 2.0 |
| Propyleneglycol USP | balance |
| Citric Acid USP | 1.5 |
| Flavoring | balance |
| Coloring | balance |
| Distilled Water | balance |

The composition according to the present invention is effective in treating all the major symptoms of PMS by provide a broad therapeutic spectrum. Each of the active ingredients will address certain of the PMS symptoms. The overlapping nature of the active ingredients within the method and composition of the present invention enhances the effectiveness of treatment while at the same time compensating for deficiencies of a particular ingredient.

For example, the magnesium will provide the greatest relief for water retention and negative affect. By itself, it has virtually no effect on the remaining symptoms. Conversely, although calcium provides a broad-based treatment for every one of the symptoms; "negative affect" and water retention are only somewhat improved. However, by combining calcium and magnesium according to the present method and formulation, symptoms such as cramping and back pain are fully addressed while an overall synergistic improvement in treatment is achieved with respect to negative affect. The analgesic component fills the remaining gaps in treatment, especially in regard to pain, headache and soreness while the diuretic targets water retention and its related symptoms. Thus, a broad-based therapeutic spectrum is achieved having improvements over the prior art methods and formulations.

Applicant believes that the present combination of active ingredients and method steps, especially those designed to address the same symptoms, produce a synergistic improvement in therapy over the individual ingredients alone. Since the applicant has selected active ingredients designed to address each of the various symptoms through different mechanisms of action, their cumulative effect produces improved treatment.

The formulation of the present invention may be incorporated within any suitable carrier known in the art, for example sucrose or dextrose. It may be in tablet or capsule form, in chewable or effervescent tablet or in liquid form. Further, the formulation may be prepared as a sustained release capsule or tablet with the concentration of the active ingredients being that for the total daily dosage.

While this invention has been described as having a preferred designs, it is understood that it is capable of further modifications, uses and/or adaptations of the invention following in general the principle of the invention and including such departures from the present disclosure as come within the known or customary practice in the art to which the invention pertains and as may be applied to the central features hereinbefore set forth, and fall within the scope of the invention and of the limits of the appended claims.

I claim:

1. A therapeutic composition for the treatment of premenstrual syndrome comprising an effective amount of:
   a) calcium;
   b) magnesium;
   c) acetaminophen; and
   d) pamabrom.

2. A therapeutic composition according to claim 1 wherein the calcium is present in a compound selected from the group consisting of calcium carbonate, calcium chloride, calcium glucoheptonate, calcium gluconate, calcium gluconogalactogluconate, calcium lactate, calcium phosphate dibasic anhydrous, calcium phosphate dibasic dihydrate and calcium phosphate tribasic.

3. A therapeutic composition according to claim 1 wherein the magnesium is present in a compound selected from the group consisting of magnesium glucoheptonate, magnesium pyrrolidone carboxylic acid, magnesium gluconate, and magnesium sulfate.

4. A therapeutic composition according to claim 1 wherein:
   a) said calcium is present from about 27.2 to about 40.8 percent by weight of the composition;
   b) said magnesium is present from about 9.2 to about 13.8 percent by weight of the composition;
   c) said acetaminophen is present from about 40 to 60 percent by weight of the composition; and
   d) said pamabrom is present from about 3.2 to about 4.8 percent by weight of the composition.

5. A therapeutic composition according to claim 1 wherein:
   a) the calcium is present as calcium carbonate from about 45.33 to 102 percent by weight of the acetaminophen;
   b) the magnesium is present as magnesium gluconate from about 15.33 to 34.5 percent by weight of the acetaminophen; and
   c) the pamabrom is present from about 4.5 to 13.25 percent by weight of the acetaminophen.

6. A method for relief of premenstrual syndrome comprising administering to a patient in need of relief of premenstrual syndrome an effective amount of calcium, magnesium, acetaminophen and pamabrom so that the symptoms of premenstrual syndrome are reduced.

7. A method according to claim 6 wherein:
   a) the effective amount of calcium is about 1200 mg per day;
   b) the effective amount of magnesium is about 400 mg per day;
   c) the effective amount of acetaminophen is about 2000 mg per day; and
   d) the effective amount of pamabrom is about 100 mg per day.

8. A method according to claim 6 wherein the calcium, magnesium, acetaminophen and pamabrom are administered orally.

9. A method according to claim 8 wherein the calcium is administered in the form of a compound selected from the group consisting of calcium carbonate, calcium chloride, calcium glucopheptonate, calcium gluconate, calcium gluconogalactogluconate, calcium lactate, calcium phosphate dibasic anhydrous, calcium phosphate dibasic dihydrate and calcium phosphate tribasic.

10. A method according to claim 8 wherein the magnesium is administered in the form of a compound selected from the group consisting of magnesium glucoheptonate, magnesium pyrrolidone carboxylic acid, magnesium gluconate, and magnesium sulfate.

* * * * *

UNITED STATES PATENT AND TRADEMARK OFFICE
CERTIFICATE OF CORRECTION

PATENT NO.  : 5,612,061
DATED       : March 18, 1997
INVENTOR(S) : Simon W. Rabkin It is certified that error appears in the above-indentified patent and that said Letters Patent is hereby corrected as shown below:

On the cover page, insert the following:

-- [73] Assignee: NeoTech MI. International, Inc., Richmond, B.C., Canada-- and following "Primary Examiner-John Pak" insert

--Attorney, Agent, or Firm-Heslin & Rothenberg, P.C.--

Signed and Sealed this

Thirtieth Day of September, 1997

Attest:

BRUCE LEHMAN

Attesting Officer

Commissioner of Patents and Trademarks